US012668610B2

(12) United States Patent
Guo et al.

(10) Patent No.: US 12,668,610 B2
(45) Date of Patent: Jun. 30, 2026

(54) COMPOUNDS FOR DRUG DELIVERY ACROSS BLOOD-BRAIN BARRIER

(71) Applicant: University of Houston System, Houston, TX (US)

(72) Inventors: Bin Guo, Sugar Land, TX (US); Damith Gomika Udugamasooriya, Katy, TX (US); Xinli Liu, Sugar Land, TX (US); Satya Prakash Shukla, Houston, TX (US); Kwang Bog Cho, Houston, TX (US); Xue Zhou, Houston, TX (US)

(73) Assignee: UNIVERSITY OF HOUSTON SYSTEM, Houston, TX (US)

( * ) Notice: Subject to any disclaimer, the term of this patent is extended or adjusted under 35 U.S.C. 154(b) by 718 days.

(21) Appl. No.: 18/011,649

(22) PCT Filed: Jun. 22, 2021

(86) PCT No.: PCT/US2021/038408

§ 371 (c)(1),
(2) Date: Dec. 20, 2022

(87) PCT Pub. No.: WO2022/005807

PCT Pub. Date: Jan. 6, 2022

(65) Prior Publication Data

US 2023/0257420 A1 Aug. 17, 2023

Related U.S. Application Data

(60) Provisional application No. 63/047,440, filed on Jul. 2, 2020.

(51) Int. Cl.
*C07K 7/06* (2006.01)
*A61K 47/64* (2017.01)
*A61P 25/00* (2006.01)

(52) U.S. Cl.
CPC .............. *C07K 7/06* (2013.01); *A61K 47/645* (2017.08); *A61P 25/00* (2018.01)

(58) Field of Classification Search
None
See application file for complete search history.

(56) References Cited

U.S. PATENT DOCUMENTS

2018/0156826 A1* 6/2018 German ............. G01N 33/6896

FOREIGN PATENT DOCUMENTS

WO 2003/049772 6/2003
WO 2017/015644 1/2017

OTHER PUBLICATIONS

Matharage et al. ('Unbiased selection of peptide-peptoid hybrids specific for lung cancer compared to normal lung epithelial cells' ACS Chemical Biology v10 2015 pp. 2891-2899) (Year: 2015).*

Appleby B (from the Merck Manual 'Overview of prion diseases' dated Jul. 2024 pp. 1-5, retrieved from https://www.merckmanuals.com/home/brain-spinal-cord-and-nerve-disorders/prion-diseases/overview-of-prion-diseases on Nov. 4, 2025, 5 pages) (Year: 2024).*

Johnsen et al. ('Targeting the transferrin receptor for brain drug delivery' Progress in Neurobiology v181 2019 pp. 1-30) (Year: 2019).*

Pilozzi et al. ('Overcoming Alzheimer's disease stigma by leveraging artificial intelligence and blockchain technologies' Brain Sciences v10 2020 pp. 1-13) (Year: 2020).*

Notification of International Search Report and The Written Opinion of the International Search Authority—The European Patent Office—mailed Nov. 26, 2021 for PCT/US21/38408, 15 pages.

Tan, et al., "High-throughput evaluation of relative cell permeability between peptoids and peptides", Bioorganic & Medicinal Chemistry, vol. 16, 2008, pp. 5853-5861.

Murphy, et al., "A combinatorial approach to the discovery of efficient cationic peptoid reagents for gene delivery", Proceedings of the National Academy of Sciences, National Academy of Sciences, vol. 95, No. 4, Feb. 17, 1998, pp. 1517-1522.

Wender, et al., "The design, synthesis, and evaluation of molecules that enable or enhance cellular uptake: Peptoid molecular transporters", Proceedings of the National Academy of Sciences, National Academy of Sciences, vol. 97, No. 24, Nov. 21, 2000, pp. 13003-13008.

Pradhan, et al., "Discovery of Neuroregenerative Peptoid from Amphibian Neuropeptide that inhibits Amyloid-ß Toxicity and Crosses Blood-Brain Barrier", ACS Chemical Neuroscience, vol. 10, No. 3, Mar. 20, 2019, pp. 1355-1368.

Notification of Transmittal of International Preliminary Report on Patentability mailed from the International Bureau of WIPO on Jan. 12, 2023 for PCT/US21/38408, 8 pages.

* cited by examiner

*Primary Examiner* — Ronald T Niebauer
(74) *Attorney, Agent, or Firm* — Jackson Walker LLP

(57) ABSTRACT

Compounds disclosed herein have been shown to bind to the transferrin receptor making them capable of crossing the blood-brain barrier (BBB) and useful for treating diseases or disorders of the brain, such as cancer, ischemic stroke, Alzheimer's disease, or Parkinson's disease.

2 Claims, 12 Drawing Sheets

Specification includes a Sequence Listing.

A.
TRBP6

B.
TRBP3

C.
TRBP5

KD: siRNA knockdown; CT: WT transferrin receptor.

A

B

C

D

COMPOUNDS FOR DRUG DELIVERY ACROSS BLOOD-BRAIN BARRIER

This application claims priority to U.S. Provisional Patent Application No. 63/047,440, entitled "Compounds for Drug Delivery Across Blood-Brain Barrier," filed Jul. 2, 2020, the entire contents of which are hereby incorporated by reference.

BACKGROUND

This disclosure pertains to compounds useful for drug delivery across the blood-brain barrier.

Diseases in the brain are difficult to treat. These include cancer metastasis to the brain (such as lung cancer, breast cancer, etc.), ischemic stroke, Alzheimer's disease, and Parkinson's disease. The brain is protected from the periphery by the blood-brain barrier (BBB), which consists of endothelial cells that interconnect tightly through tight junction proteins. Most drugs cannot cross the BBB to enter the brain, thus many diseases in the brain are difficult to treat. A variety of methods have been tried to deliver drugs across BBB by targeting the transferrin receptor. The transferrin receptor is responsible for the transport of iron into the brain. Antibodies have been developed to bind to the transferrin receptor. These antibodies were conjugated with drugs to deliver them into the brain. However, the antibodies have suffered drawbacks in low delivery efficiency and are associated with toxicities.

SUMMARY

The present disclosure relates generally to compounds capable of crossing the blood-brain barrier (BBB) and their uses for drug delivery.

Generally, the present disclosure relates to compounds shown to cross the BBB and having the structures shown in FIG. 1. FIG. 1 shows (A) Chemical structure of TRBP6, (B) Chemical structure of TRBP3, and (C) Chemical structure of TRBP5, in accordance with preferred embodiments.

The present disclosure also relates to drug delivery agents and compositions comprising the compounds shown to cross the BBB disclosed herein and methods for drug delivery comprising the compounds shown to cross the BBB disclosed herein.

DETAILED DESCRIPTION OF PREFERRED EMBODIMENTS

The present disclosure relates to compounds shown to cross the blood-brain barrier (BBB) and their uses in drug delivery.

Accordingly, preferred embodiments disclosed herein relate to compounds capable of crossing the blood-brain barrier having the structures shown below:

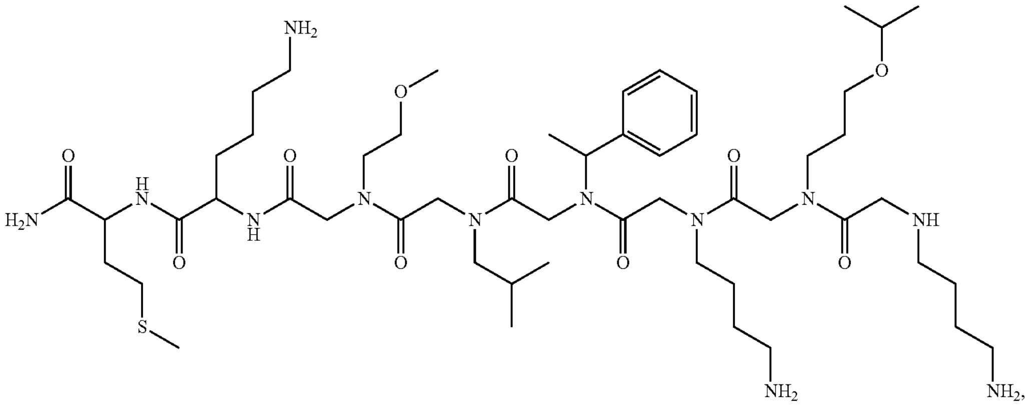

,

-continued

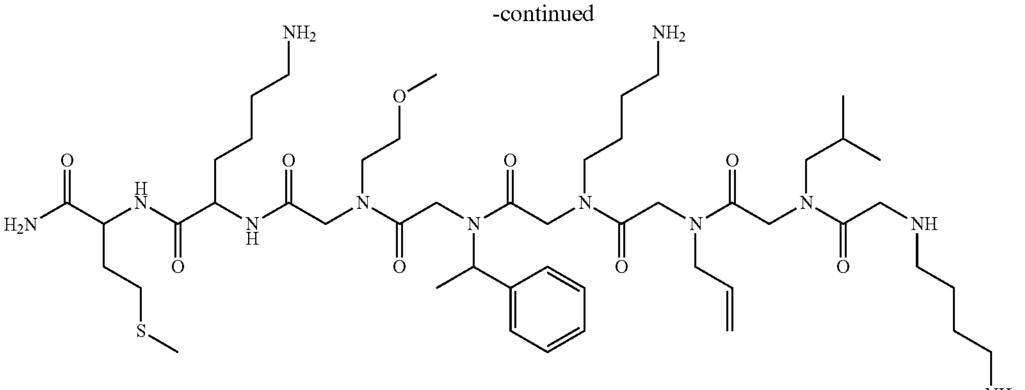

NH2, and

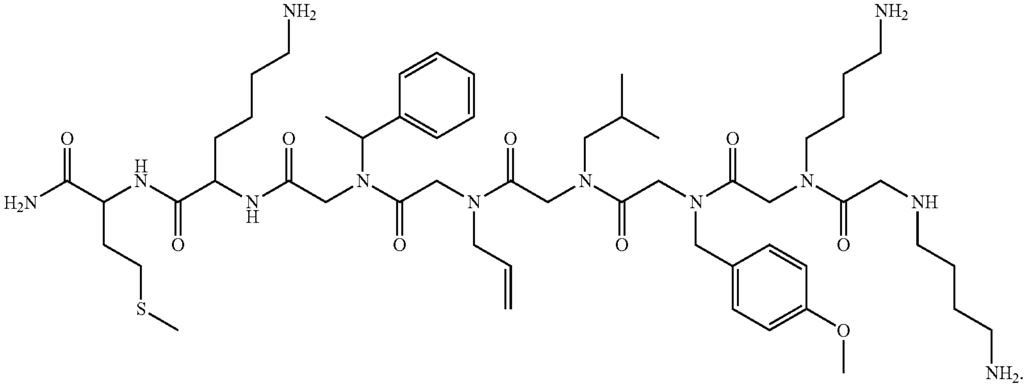

Figure 2:
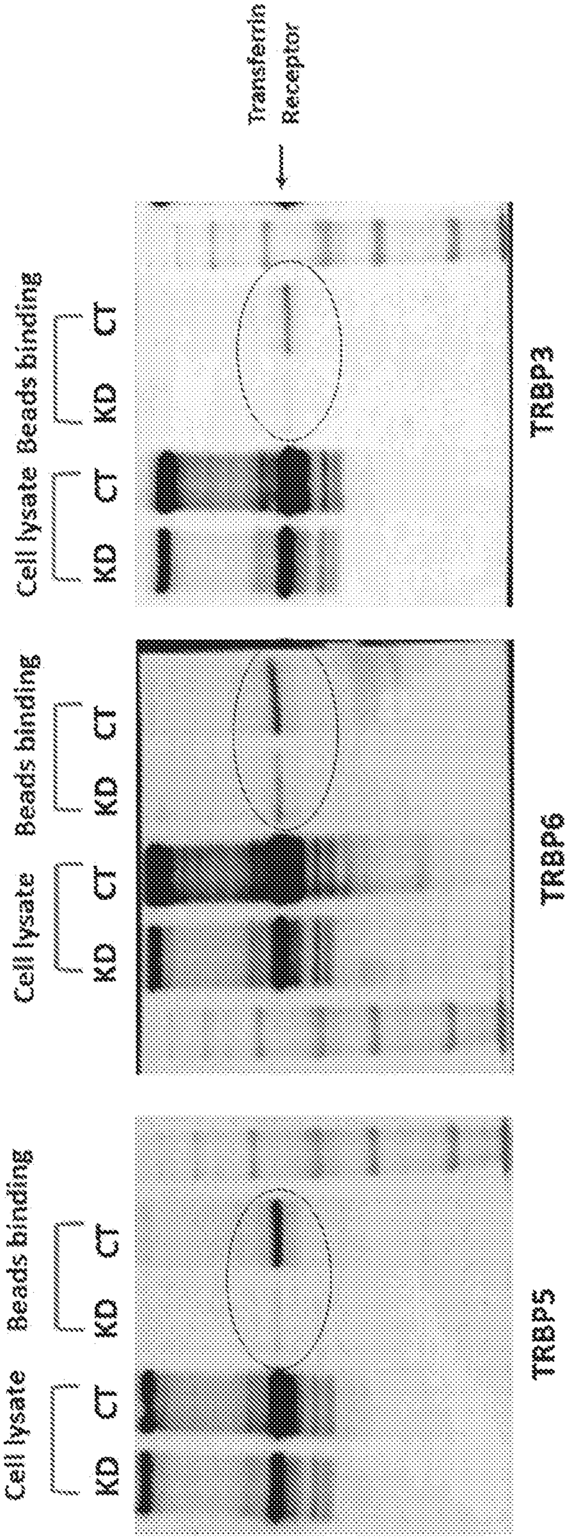
FIG. 2 show results of a pull-down assay confirming binding of exemplary compounds to transferrin receptor.

The binding of three exemplary compounds to the transferrin receptor was confirmed in a pull-down assay. Results are shown in FIG. 2. Cell lysates from transferrin receptor positive or negative HeLa cells were extracted using RIPA buffer, and subsequently incubated with TRBP3, TRBP5, or TRBP6 conjugated beads at 4° C. overnight. The beads were then washed with RIPA buffer for 3 times, and the binding proteins were eluted with 1% SDS. The yielded lysates were then applied onto 10% SDS-PAGE gel and subjected to western blotting analysis with antibody against transferrin receptor.

Figure 3:
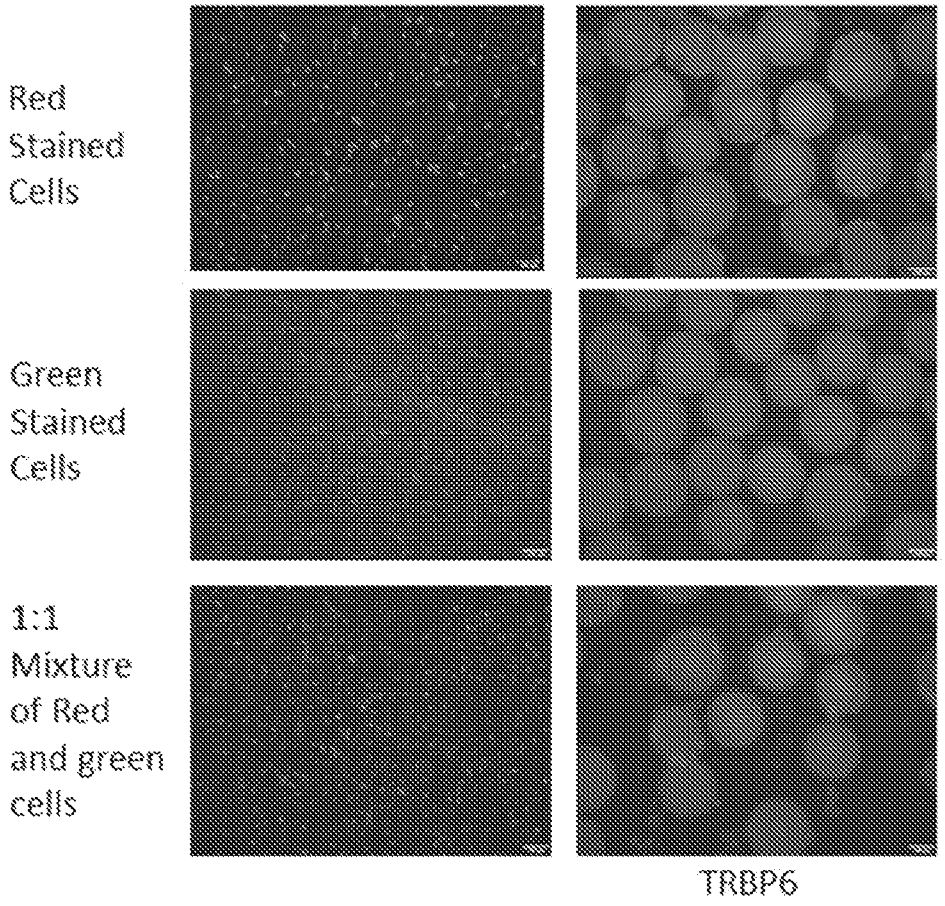
FIG. 3 shows binding of an exemplary compound (TRBP6) resynthesized on tentagel beads to transferrin receptor expressing HeLa cells but not to transferrin receptor negative cells.

The on-bead two-color combinatorial cell-screening was validated by resynthesizing the compounds on tentagel beads and incubating them with transferrin receptor positive HeLa cells and transferrin receptor negative Hela cells separately as well as a mixture of these cells. The beads specifically bound with the transferrin receptor positive HeLa cells. Results are shown in FIG. 3, with the cells shown on the left column and the beads containing TRBP6 after incubation with the cells shown in the right column.

Figure 4:
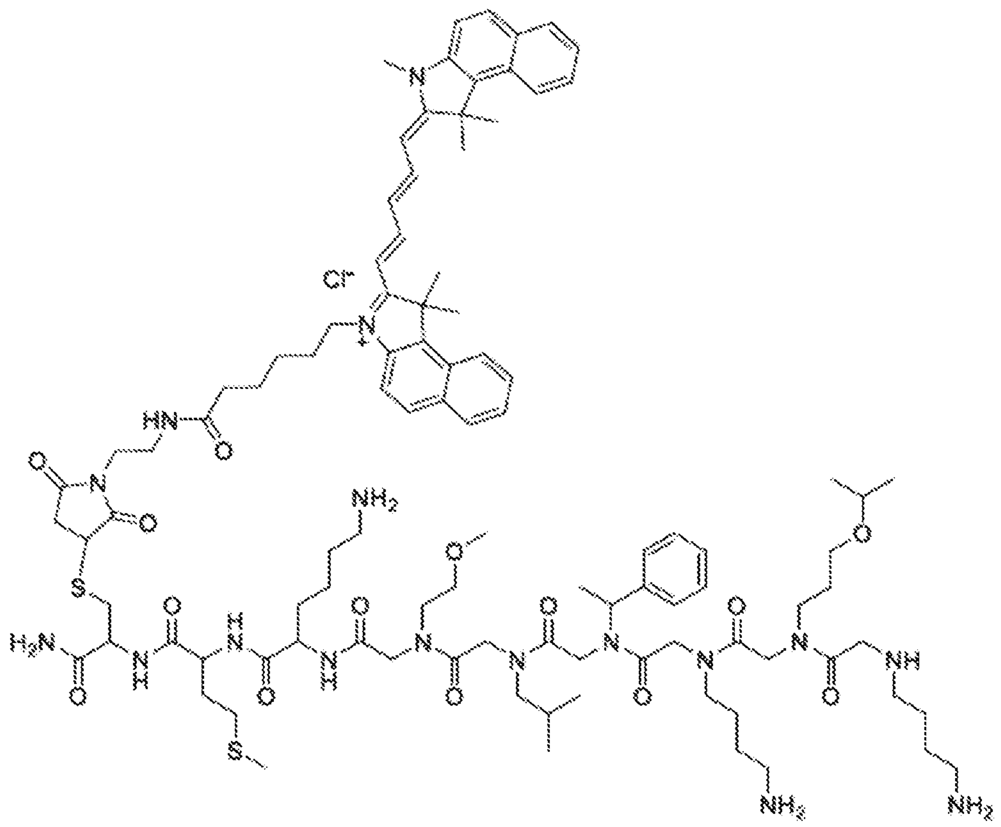
FIG. 4 shows chemical structure of Cy5.5-TRBP6.

The activity of these compounds to deliver Cy5.5 fluorescent dye into the brains of mice was investigated. FIG. 4 shows the chemical structure of the peptoid Cy5.5-TRBP6. The Cy5.5 labeled peptoids or Cy5.5-Ang peptide were injected intravenously to CD-1 mice (25 nmol/mouse, n=4 per compound) and imaged using IVIS imager. The mice were sacrificed at 30 minutes, the heart was perfused with 10 mL of PBS, blood and organs were collected for ex vivo imaging. As shown in FIGS. 5-8, the compounds TRBP3, TRBP5, and TRBP6 effectively delivered Cy5.5 into the brain. The efficacy of TRBP6 brain delivery is much higher than other compounds, including the well-studied Angiopep-2 (Ang) peptide.

Additional preferred embodiments relate to derivatives of the three exemplary compounds capable of crossing the BBB. Potential derivatives include dimers, trimers, tetramers, and cylic dimers of the compounds, such as those shown in FIG. 9 for TRBP6.

The exemplary compounds capable of crossing the BBB described herein may occur in different geometric and enantiomeric forms, and both pure forms and mixtures of these separate isomers are included in the scope of this invention, as well as any physiologically functional or pharmacologically acceptable salt derivatives or prodrugs thereof. Production of these alternate forms would be well within the capabilities of one skilled in the art.

The current invention also pertains to drug delivery compositions comprising an exemplary compound capable of crossing the BBB as described herein that is linked to a drug or therapeutic agent. The current invention also pertains to methods of delivering a drug or therapeutic agent across the BBB, including the step of linking an exemplary compound capable of crossing the BBB as described herein to a drug or therapeutic agent to produce an exemplary drug delivery composition, then administering the exemplary drug delivery composition to a subject in accordance with preferred embodiments disclosed herein. In preferred embodiments, the drug or therapeutic agent may be useful for the prevention or treatment of a disease or disorder of the brain, such as cancer, ischemic stroke, Alzheimer's disease, and Parkinson's disease.

In another aspect of the present invention there is provided a pharmaceutical composition including a therapeutically effective amount of an exemplary drug delivery composition in accordance with preferred embodiments disclosed herein, comprising an exemplary compound capable of crossing the BBB as described herein linked to a drug or therapeutic agent, and a pharmaceutically acceptable excipient, adjuvant, carrier, buffer or stabilizer. A "therapeutically effective amount" is to be understood as an amount of an exemplary drug delivery composition that is sufficient to show preventative or therapeutic effects on a disease or disorder of the brain. The actual amount, rate and time-course of administration will depend on the disease or disorder, the subject, and the nature and severity of the effects. Prescription of treatment is within the responsibility of general practitioners and other medical doctors. The pharmaceutically acceptable excipient, adjuvant, carrier, buffer or stabiliser should be non-toxic and should not interfere with the efficacy of the active ingredient. The precise nature of the carrier or other material will depend on the route of administration, which may be oral, sublingual, intranasal, or by injection, such as cutaneous, subcutaneous, or intravenous injection, or by dry powder inhaler.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such as gelatin. For intravenous, cutaneous or subcutaneous injection, the active ingredient will be in the form of a parenterally acceptable aqueous solution which is pyrogen-free and has a suitable pH, isotonicity and stability. Those of relevant skill in the art are well able to prepare suitable solutions using, for example, isotonic vehicles such as sodium chloride solution, Ringer's solution, or lactated Ringer's solution. Preservatives, stabilizers, buffers, antioxidants and/or other additives may be included as required.

In another aspect, there is provided the use in the manufacture of a medicament of a therapeutically effective amount of an exemplary drug delivery composition for delivery of a drug or therapeutic agent across the BBB as defined above for administration to a subject.

The term "pharmacologically acceptable salt" used throughout the specification is to be taken as meaning any acid or base derived salt formed from hydrochloric, sulfuric, phosphoric, acetic, citric, oxalic, malonic, salicylic, malic, fumaric, succinic, ascorbic, maleic, methanesulfonic, isoethonic acids and the like, and potassium carbonate, sodium or potassium hydroxide, ammonia, triethylamine, triethanolamine and the like.

The term "prodrug" means a pharmacological substance that is administered in an inactive, or significantly less active, form. Once administered, the prodrug is metabolised in vivo into an active metabolite.

The term "therapeutically effective amount" means a nontoxic but sufficient amount of the drug to provide the desired therapeutic effect. The amount that is "effective" will vary from subject to subject, depending on the age and general condition of the individual, the particular concentration and composition being administered, and the like. Thus, it is not always possible to specify an exact effective amount. However, an appropriate effective amount in any individual case may be determined by one of ordinary skill in the art using routine experimentation. Furthermore, the effective amount is the concentration that is within a range sufficient to permit ready application of the formulation so as to deliver an amount of the drug that is within a therapeutically effective range.

Further aspects of the present invention will become apparent from the following description given by way of example only.

EXAMPLE 1

Figure 1:
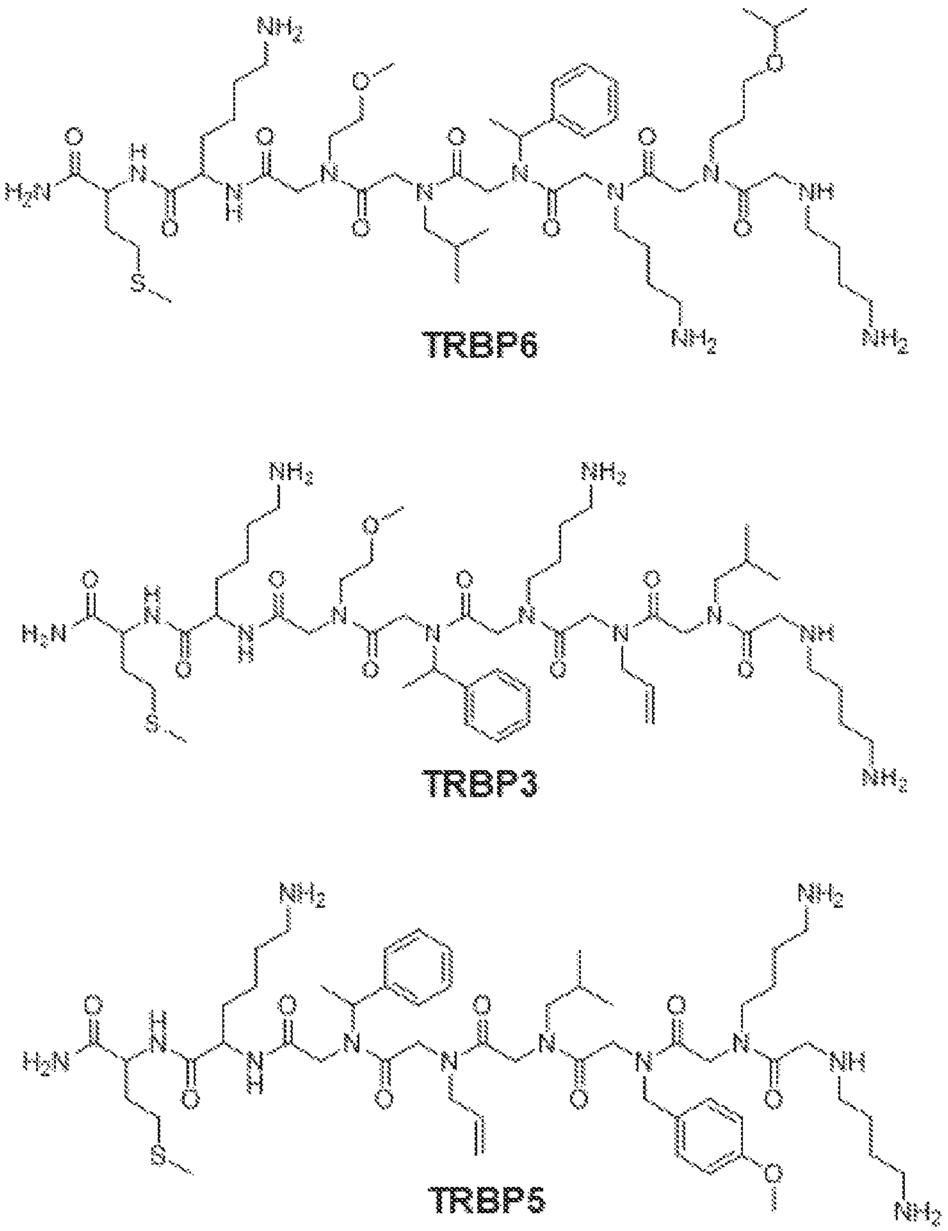
FIG. 1 shows (A) Chemical structure of TRBP6, (B) Chemical structure of TRBP3, and (C) Chemical structure of TRBP5, in accordance with preferred embodiments described herein.

The small molecule compounds shown in FIG. 1 that bind to the transferrin receptor were identified by performing an on-bead two-color (OBTC) combinatorial cell-screening with the peptoid library.

Chemicals and Reagents.

TentaGel MB $NH_2$ resin (particle size: 140-170 μm, loading capacity: 0.2-0.3 mmol/g, 520,000 beads/g) was purchased from Rapp Polymere GmbH (Tuebingen, Germany). Rink amide resin, (particle size: 100-200 mesh, loading capacity: 0.3-0.6 mmol/g) was purchased from Chem-Impex International, Inc. (Wood Dale, IL, USA). All Fmoc-protected amino acids and 2-(1H-Benzotriazole-1-yl)-1,1,3,3-tetramethyluronium hexafluorophosphate (HBTU), Hydroxybenzotriazole (HOBt), all primary amines, bromoacetic acid, N,N-diisopropylcarbodiimide (DIC), N,N-diisopropylethylamine (DIPEA), piperidine, trifluoroacetic acid (TFA), cyanogen bromide (CNBr), Triisopropylsialine (TIS), α-cyano-4-hydroxycinnamic acid, acetonitrile (ACN), hydrochloric acid (HCl), dichloromethane (DCM) and N,N-dimethylformamide (DMF), were obtained from MilliporeSigma (Massachusetts, MA, USA). GIBCO enzyme free cell dissociation buffer and Qtracker Cell Labeling Kits were obtained from ThermoFisher Scientific (Waltham, MA USA). Angiopep-2 peptide (Ang) with a terminal cysteine (TFFYGGSRGKRNNFKTEEYC) (SEQ ID NO:1) was custom made at ChinaPeptides. Cyanine5.5 maleimide was purchased from Lumiprobe. All chemical reagents and solvents from commercial sources were used without further purification. Five-ml disposable reaction columns (Intavis AG, Tuebingen, Germany) were used as reaction vessels for solid-phase synthesis. Syntheses of peptoids under microwave conditions were performed in a 1000 W microwave oven with 10% power. All purifications were completed on a Waters HPLC system (Waters Corporation, MA, USA). Mass spectra were recorded on an Applied Biosystems Voyager DE Pro mass spectrometer using α-cyano-4-hydroxycinnamic acid as the matrix.

Library Synthesis.

The basic structure of the library consists of two amino acids followed by 6-mer diversified peptoid region. TentaGel MB $NH_2$ 6 g (140-170 μm; substitution: 0.2-0.3 mmol/g resin; Rapp Polymere, Germany) were swelled in DMF for 30 min at room temperature in a 5 ml reaction column (200 mg of resin in each column) The DMF was drained from the reaction vessels the resin was first coupled to Fmoc-Met-OH (5.0 equiv) using 5.0 equiv HBTU and 5.0 equiv HOBt as coupling reagents in the presence of 10.0 equiv of DIPEA for overnight shaking. Fmoc group was removed by treating the resins with 20% piperidine in DMF twice for 10 minutes. After washing the resins, Fmoc-Lys(Boc)-OH was added (for 2.0 hours reaction time) and Fmoc group was removed as described previously. The rest of the synthesis was achieved using the split-pool synthesis protocol. Total 10 different amines were chosen for the library are N-Boc-1,4-butanediamine, allylamine, isobutylamine, 2-methoxyethylamine, 3-isopropoxypropylamine, β-alanine, (R)-(+)-α-methylbenzylamine, 4-methoxybenzylamine, piperonylamine and furfurylamine. The resins were equally distributed into 10 batches (30 reaction columns) for microwave assisted peptoid synthesis steps. Each of the reaction vessels were treated with 1.0 M Bromoacetic acid in anhydrous DMF (1.0 ml) and 1.5 M DIC in anhydrous DMF (1.0 ml), gently shaken for 30 seconds and microwaved (1000 W) for 15 seconds with the power set at 10%. The beads were shaken again for 30 seconds and microwaved another round as described above. The reaction columns were drained and washed with DMF (2.0 ml×10 times). Then each of the reaction batch was treated with 1.0 ml of 2.0 M solution of the primary amines (3 reaction columns (1 batch) per amine) and was put on shaker for 2.0 hours at 25° C. The resins were washed, pooled and divided again equally into 10 batches (30 reaction columns) and subjected to addition of next peptoid residue. This procedure was repeated until 6-mer peptoid region was completed. At the end of synthesis, the beads were washed with DCM (2.0 ml×3 times), and treated with 2.5 ml of 95% TFA, 2.5% water and 2.5% TIS on the shaker for 2 hours to remove the side chain protection and were neutralized with 10% diisopropylethylamine in DMF. Reaction vessel was drained, washed with DMF (2.0 ml×3 times) and stored in anhydrous DMF at 4° C.

Cells and siRNA Transduction.

The cell line HeLa were purchased from American Type Culture Collection. HeLa cells were maintained in Dulbecco's Modified Eagle's Medium (Corning) supplemented with 100 units/ml penicillin, 100 μg/ml streptomycin, and 10% fetal bovine serum (Corning) at 37° C. with 5% $CO_2$. For siRNA transfection, HeLa cells were seeded ($2.5\times10^6$/dish) in 10 cm cell culture dish one day before transfection, and treated with human TFRC siRNA (Dharmacon, Cat #M-003941-02-0010) for 24 hours with X-tremeGENE siRNA transfection reagent (Roche) according to the manufacturer's instructions.

On Bead Two Color Binding Assay for Combinatorial Library Screen.

Nearly 50,000 peptoid library beads were washed two times in DMEM medium containing 10% FBS (media) and then incubated in 1.0 ml (DMEM+10% FBS) for 1.0 hour in a polypropylene tube. Transferrin receptor positive HeLa cells and transferrin receptor negative HeLa cells were removed from culture plates with GIBCO enzyme free cell dissociation buffer 2.0 ml per plate for 20 minutes at 37° C. Cells were washed and suspended in DMEM+10% FBS media. Cells were counted and distributed in 1.5 ml microcentrifuge tubes with $1.0\times10^6$ cells in 1.0 ml of media. Then the cell labeling procedure was conducted as follows: 1.0 μl each of Qtracker reagent A and B were mixed in a 1.5 ml microcentrifuged tubes and incubated for 5.0 minutes at room temperature. 0.2 ml of media was added to each tube and vortexed for 30 seconds. $1.0\times10^6$ cells were added to each tube containing the labeling solution and incubated at 37° C. for 60 minutes. Transferrin receptor positive HeLa cells were labeled with Qtracker 655 (red color) and transferrin receptor negative HeLa cells labeled with Qtracker 565 (green color). Cells were washed twice and suspended in DMEM+10% FBS media. Labeled cells were visualized with long-pass filter of BX-51 fluorescence microscope (Olympus, PA) with a color camera. Both cell types were mixed thoroughly and pipetted up and down several times to break the clumps. 2.0 ml of cell suspension mixture was added to the tube containing 50,000 beads and incubated at room temperature with gentle shaking for 1.0 hour. During incubation, cell binding to the beads were checked time to time at about 15 minutes intervals to make sure not to over equilibrate, which could increase non-specific binding of cells to the beads. The beads were gently washed two times with DMEM+10% FBS media and visualized under the fluorescent microscope using long-pass filter.

Isolation and Preparation of Beads for Sequencing.

Single bead containing fluorescently tagged red cells was identified using a fluorescent microscope under 10× objective magnification and removed manually with a 20 μl pipette with medium size pipette tips. Selected beads were washed three times with 1.0% SDS and boiled in the same solution for 45 minutes to strip off bound cells and proteins. Finally the beads were washed three times with water. To cleave the compound from the bead and prepare it for MS/MS sequencing cleaving solution was prepared, for that: 30 μl of CNBr (5.0 M in ACN) was added to 1.0 ml of 0.1 N HCl. 50 μl of cleaving solution was added to the 1.5 ml tube which contained the single isolated bead. The tube was incubated at 25° C. for 4.0 hours. The solution was evaporated using freeze dryer (SP Scientific, USA) and cleaved compound was suspended in 20 μl of water. MS/MS sequencing data was obtained using AB Sciex TOF/TOF 5800 machine.

Three "hits" were identified in this screening experiment. The compounds are shown in FIG. 1, with one identified as TRBP6 (transferrin receptor binding peptoid #6).

In Vitro Pull-Down Assay.

Cell lysates from HeLa cells with transferrin receptor expression or transferrin receptor knockdown were extracted using RIPA buffer (Alfa Aesar) supplemented with protease inhibitors (Roche), and subsequently incubated with TRBP6, TRBP3, and TRBP5 conjugated beads at 4° C. overnight. The beads were then washed with RIPA buffer for 3 times, and the binding proteins were eluted with 1% SDS at 95° C. for 5 mins. The yielded lysates were then mixed with 4× Laemmli Sample Buffer (loading buffer) (Bio-Rad). The samples were then applied onto 8% SDS-PAGE gel. The gels were consequently subjected to western blotting analysis.

Western Blot Analysis.

Cells were lysed in RIPA buffer (1% NP-40, 0.5% sodium deoxycholate, 0.1% SDS in PBS). Complete protease inhibitor cocktail (Roche) was added to lysis buffer before use. Protein concentration was determined by Bio-Rad DC protein assay (Bio-Rad). Protein samples were subjected to SDS-PAGE and transferred to nitrocellulose membrane. The membrane was blocked in 5% non-fat milk in PBST overnight and incubated with primary antibody and subsequently with appropriate horse radish peroxidase-conjugated secondary antibody. Signals of targeted proteins were detected by the Immun-Star HRP peroxide Luminol/Enhancer (Bio-Rad) and recorded on ChemiDoc Touch Imaging System (Bio-Rad). Anti-hTfR (human transferrin receptor) antibody was purchased from R&D system, Inc. (Cat #AF2474).

Results are shown in FIG. 2, where binding to the transferrin receptor is visible for three exemplary compounds.

Validation of on Bead Two Color Binding Screening Results.

After identifying the compound (TRBP6) with MS/MS sequencing it was resynthesized on TentaGel MB $NH_2$ beads. Three tubes of 25,000 beads (containing TRBP6 compounds) each were prepared by washing and incubating for 1.0 hour in DMEM+10% FBS. Two million cells each of transferrin receptor positive HeLa cells were stained red in color using Qtracker 655 and transferrin receptor negative HeLa cells were stained in green color using Qtracker 565 as per method described in section 4. One million transferrin receptor positive HeLa cells (red cells) were suspended in 1.0 ml of DMEM+10% FBS media and were added to a tube containing 25,000 beads. One million of transferrin receptor negative HeLa cells (green cells) were suspended in 1.0 ml of DMEM+10% FBS media and were added to another tube containing 25,000 beads. To make mixture of cells $0.5\times10^6$ of red cells and $0.5\times10^6$ green cells were mixed together and suspended in 1.0 ml of DMEM+10% FBS media were added to the third tube containing 25,000 beads. The cells were incubated with the beads for 1.0 hours at room temperature. The beads were gently washed two times with DMEM+10% FBS media and visualized under the fluorescent microscope using long-pass filter.

Results are shown in FIG. 3, with the cells shown in the left column and the beads containing TRBP6 after incubation with the cells shown in the right column. Beads only showed binding with red cells but not with green cells, thus validating the finding of the OBTC screening results.

Animals.

Female CD-1 mice (6-8 weeks old) was obtained from Charles River Laboratories and used for the tissue distribution studies. All procedures were approved by the Animal Care Operations at University of Houston and performed in accordance with the institutional guidelines for animal care and use.

Synthesis of Compound TRBP6.

TRBP6 was synthesized on Rink amide resin. 100 mg of resin was taken in 5 mL reaction column, the resin was swelled in dimethyl formamide (DMF) for 1.0 h prior to use, and Fmoc group was de-protected by treating the resin with 2.0 ml of 20% piperidine solution in DMF twice for 10 minutes each. The resin was first coupled to Fmoc-Met-OH using 5.0 equiv HBTU and 5.0 equiv HOBt as coupling reagents in the presence of 10.0 equiv of DIPEA for overnight. Fmoc were removed with the method described above. Subsequent amino acid Fmoc-Lys(Boc)-OH was introduced using the same peptide-coupling protocol (HBTU/HOBt/DIPEA), washing 10 times with DMF. After removing the Fmoc group as described above, six peptoid residues were then coupled using a two-step peptoid coupling procedure (acylation and amination) under a microwave assisted synthesis protocol. For the acylation step, beads were treated with 1.0 M bromoacetic acid (1.0 mL) and 1.5 M N,N'-Diisopropylcarbodiimide (DIC) (1.0 mL), and microwaved at 10% power (2×15 seconds) with gentle shaking in between for 30 seconds. After washing with DMF, beads were treated with 1.0 mL of 2-methoxyethylamine (2.0 M), and coupling was performed by shaking at 25° C. for 2 hours. The procedure was repeated again to attach the remaining five residues: isobutylamine, (R)-(+)-α-Methylbenzylamine, N-Boc-1,4-butanediamine, 3-Isopropoxypropylamine and N-Boc-1,4-butanediamine respectively. At the end, beads were washed with dichloromethane (DCM) and dried under vacuum before cleavage. Beads were then treated with a cleavage cocktail of TFA/$H_2O$/TIS (95%/2.5%/2.5%) for 2.0 h. The crude compound was then purified using HPLC and analyzed by MALDI-TOF.

Synthesis of Compound Cy5.5-TRBP6:

Synthesis of Cy5.5-TRBP6 was done using the similar protocol described for TRBP6. Sequence for amino acids residues for Cy5.5-TRBP6 were Fmoc-Cys(Trt)-OH, Fmoc-Met-OH and Fmoc-Lys(Boc)-OH, and the removal of Fmoc group each time was performed by treating the resin with 2.0 ml of 20% piperidine solution in DMF twice for 10 minutes each. Next, the 6 peptoid residues were coupled using the microwave-assisted synthesis protocol. The 6 peptoid sequence were 2-methoxyethylamine, isobutylamine, (R)-(+)-α-Methylbenzylamine, N-Boc-1,4-butanediamine, 3-Isopropoxypropylamine and N-Boc-1,4-butanediamine respectively. The compound was cleaved from the beads by treating with TFA/$H_2O$/TIS (95%/2.5%/2.5%) for 2.0 h. Cysteine attached TRBP6 derivative was obtained by purifying the mixture using HPLC, to this Cyanine5.5 maleimide was coupled using thiol-maleimide coupling protocol by mixing them in 1:1 equivalent ratio in water and the pH the solution was adjusted to 7. The mixture was allowed to stir for overnight at 4° C. The mixture was purified using HPLC and analyzed by MALDI-TOF to obtain Cy5.5-TRBP6.

FIG. 4 shows the chemical structure of Cy5.5-TRBP6.

Synthesis of Cy5.5-Angiopep-2 (Cy5.5-Ang):

Ang peptide was mixed with Cyanine5.5 maleimide with the molar ratio of 1:1 in water with the addition of 0.5 M EDTA. The pH of the reaction mixture was adjusted to 6.9-7.0 by hydrochloric acid (1N). The reaction was stirred at 4° C. overnight and was monitored by MALDI-TOF. Upon reaction completed, the mixture was lyophilized and purified by using preparative HPLC to give the target compound Cy5.5-Angiopep-2 (38.5%) as blue powder.

In Vivo Biodistribution Study in CD-1 Mice.

Biodistribution of Cy5.5-labeled peptoids and control Cy5.5-Ang was performed on healthy female CD-1 mice (6-8 weeks old, n=4 per group). Fluorescently labeled peptoids and Cy5.5-Ang were prepared in 100 μl saline (25 nmol of Cy5.5-TRBP in 100 μl saline per mouse) were injected intravenously via tail vein into mice. The whole body imaging of fluorescence signal was measured at 5, 15 and 30 min using the IVIS Spectrum in vivo imaging system (PerkinElmer). At 30 min, mice were euthanized and brain was perfused with 10 mL of 10% heparinized PBS at 4/ml/min flow rate via left ventricle of mice. A small incision to the right atrium was made using iris scissors before perfusion. After brain perfusion, the vital organs (brain, heart, lung, liver, spleen also blood and plasma) were collected for ex vivo imaging. The fluorescence intensity was measured at wavelength with an excitation of 660 nm and maximum emission at 710 nm. The organ region of interest (ROI) was measured and analyzed using Living image software. Data of the experiments were expressed as mean±SD and analyzed by One-way ANOVA with Dunnett's multiple comparison test. The statistical analysis was done in Graphpad Prism (Graphpad Inc., version 7.04), the results were considered statistically significant if $p<0.05$.

Statistical Analyses.

Data are expressed as mean±SEM unless noted otherwise. Data were analyzed by Student's t test and were considered statistically significant if $p<0.05$. p values are represented as precise p values or generally as *$p<0.05$, $p<0.01$, and * $p<0.001$.

Figure 5:
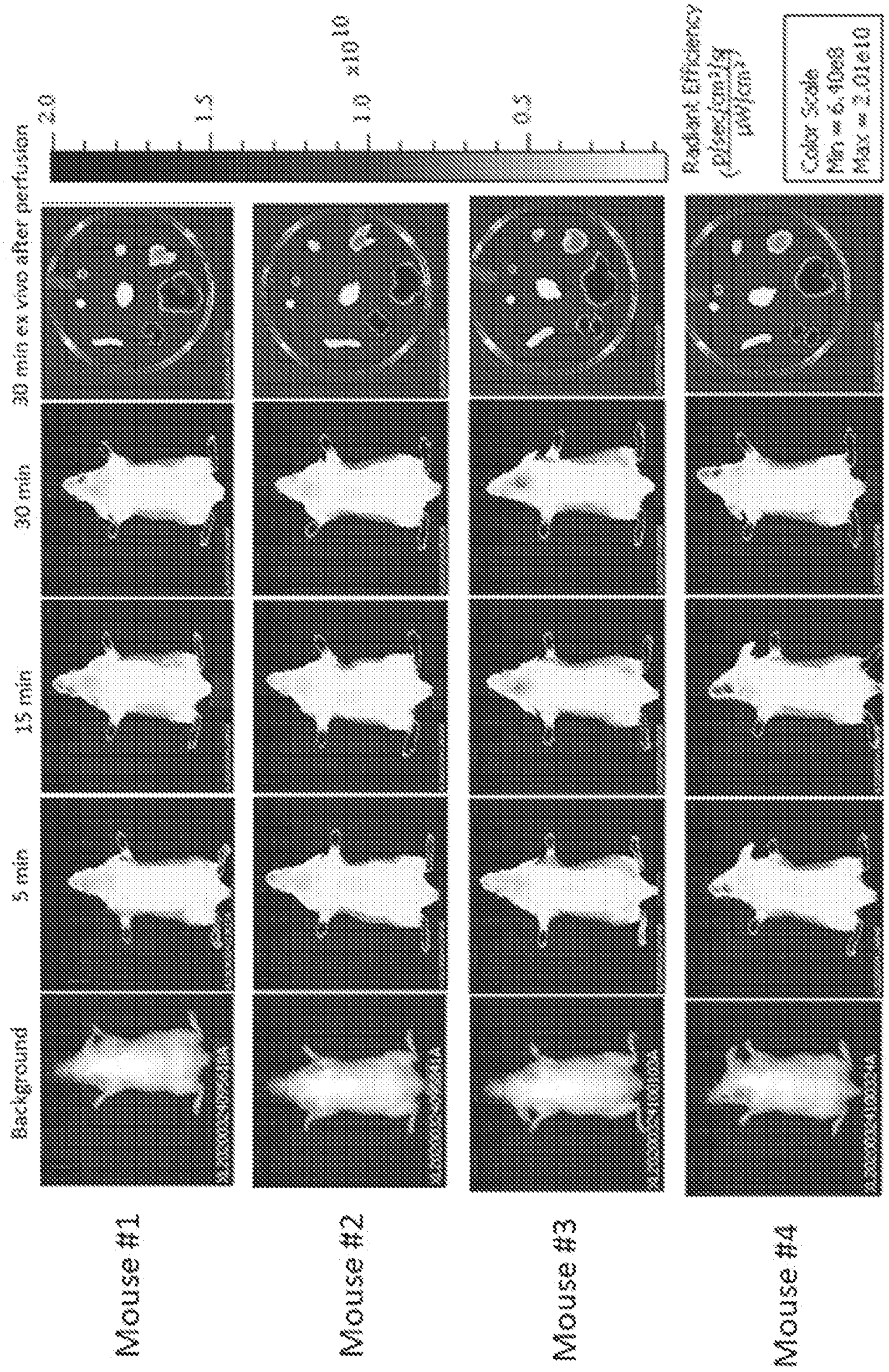
FIG. 5 shows IVIS imaging of the fluorescence intensity of mice injected with an exemplary compound capable of crossing the BBB (TRBP6) at 5, 15, and 30 minutes, and 30 minutes ex vivo after perfusion, in accordance with preferred embodiments described herein.

FIG. 5 shows IVIS imaging of the fluorescence intensity of mice injected with an exemplary compound capable of crossing the BBB, Cy5.5-TRBP6, at 5, 15, and 30 minutes, and 30 minutes ex vivo after perfusion. At 30 minutes after injection, TRBP6 showed superior efficiency than other compounds (including the well-studied Ang peptide) in brain delivery.

Figure 6:
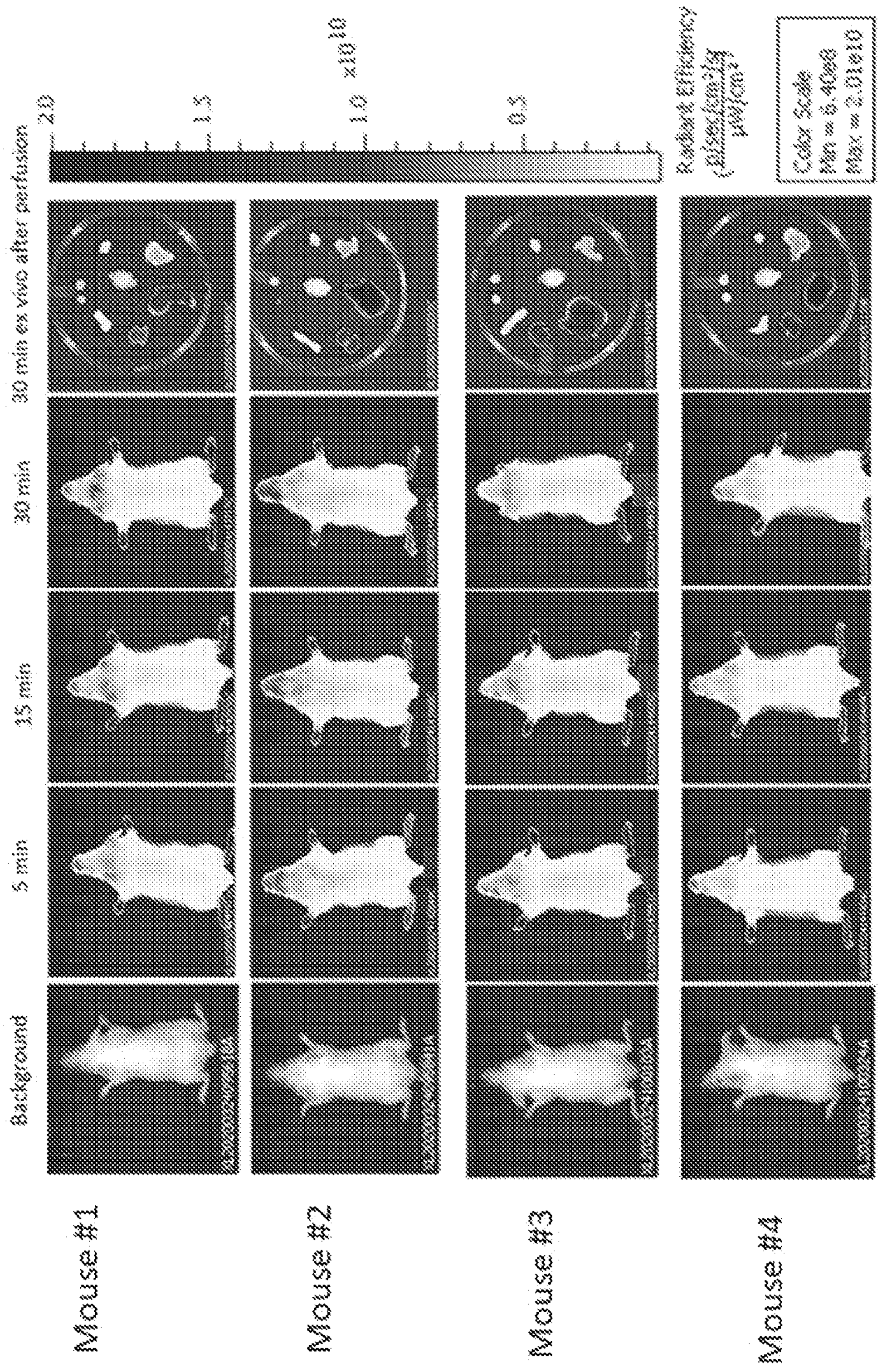
FIG. 6 shows IVIS imaging of the fluorescence intensity of mice injected with Ang peptide, at 5, 15, and 30 minutes, and 30 minutes ex vivo after perfusion.

FIG. 6 shows IVIS imaging of the fluorescence intensity of mice injected with Cy5.5-Ang peptide, at 5, 15, and 30 minutes, and 30 minutes ex vivo after perfusion.

Figure 7:
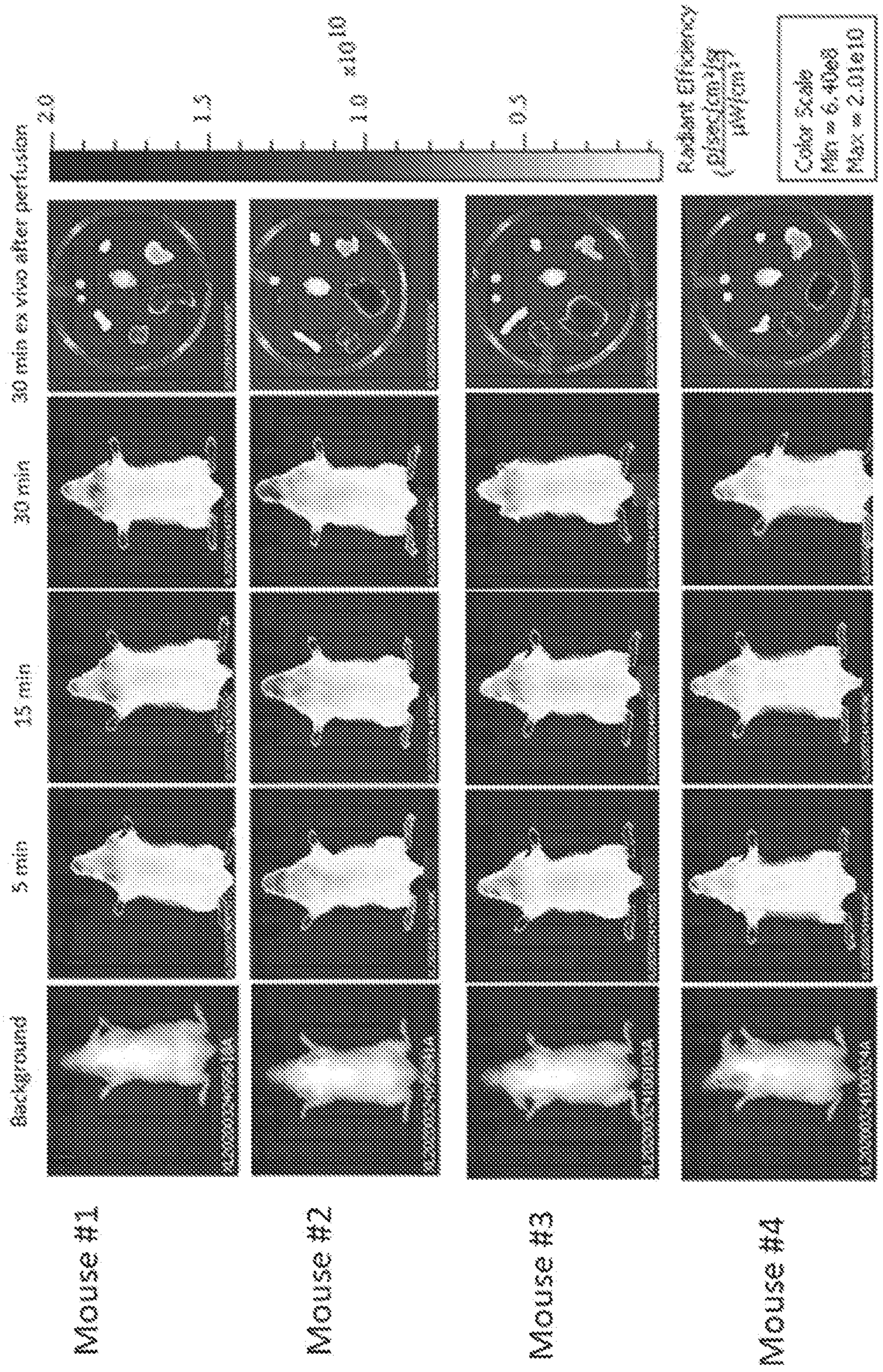
FIG. 7 shows IVIS imaging of the fluorescence intensity of mice injected with an exemplary compound capable of crossing the BBB (TRBP5) at 5, 15, and 30 minutes, and 30 minutes ex vivo after perfusion, in accordance with preferred embodiments described herein.

FIG. 7 shows IVIS imaging of the fluorescence intensity of mice injected with an exemplary compound capable of crossing the BBB, Cy5.5-TRBP5, at 5, 15, and 30 minutes, and 30 minutes ex vivo after perfusion.

Figure 8:
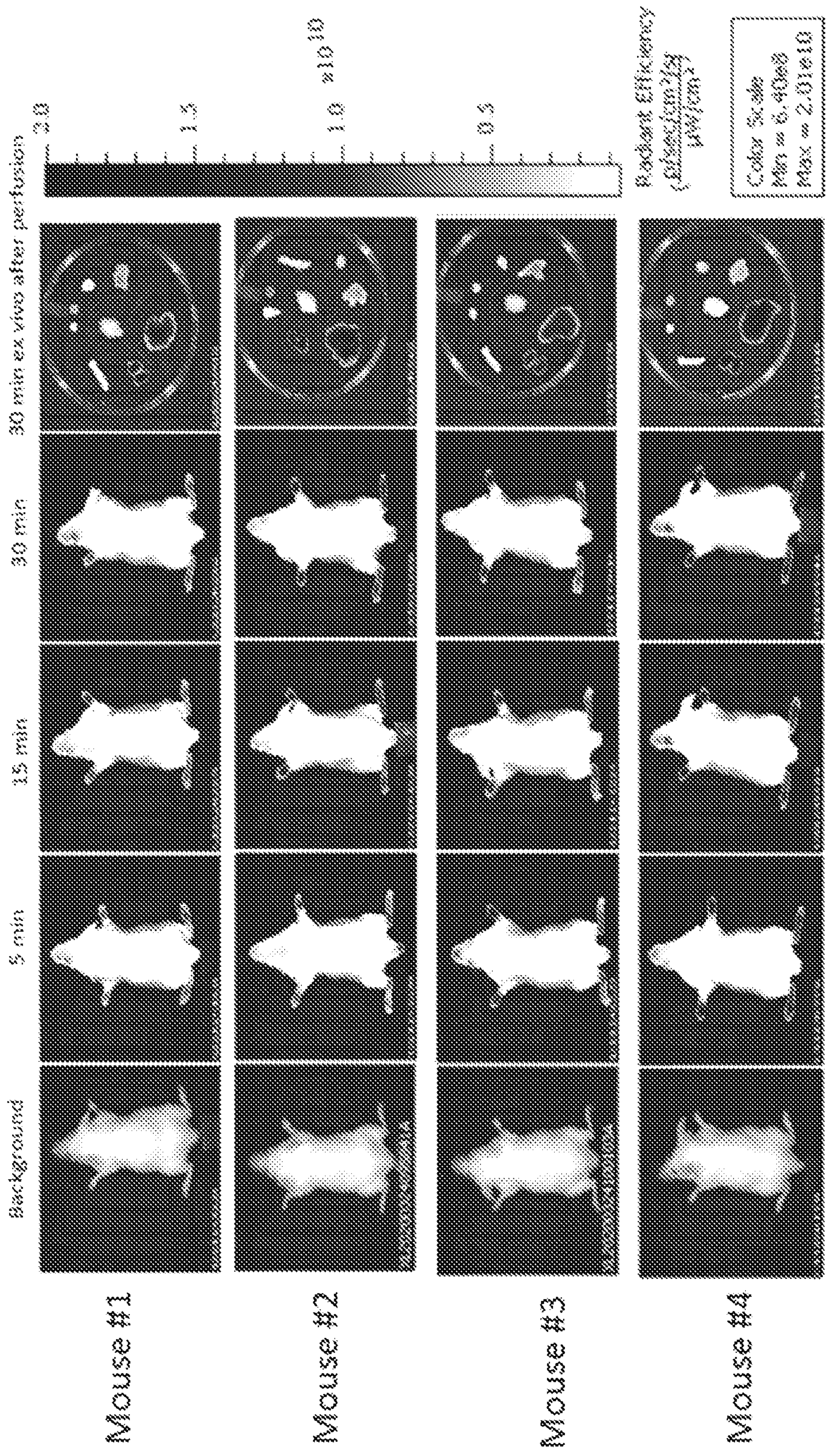
FIG. 8 shows IVIS imaging of the fluorescence intensity of mice injected with an exemplary compound capable of crossing the BBB (TRBP3) at 5, 15, and 30 minutes, and 30 minutes ex vivo after perfusion, in accordance with preferred embodiments described herein.
Figure 9A:
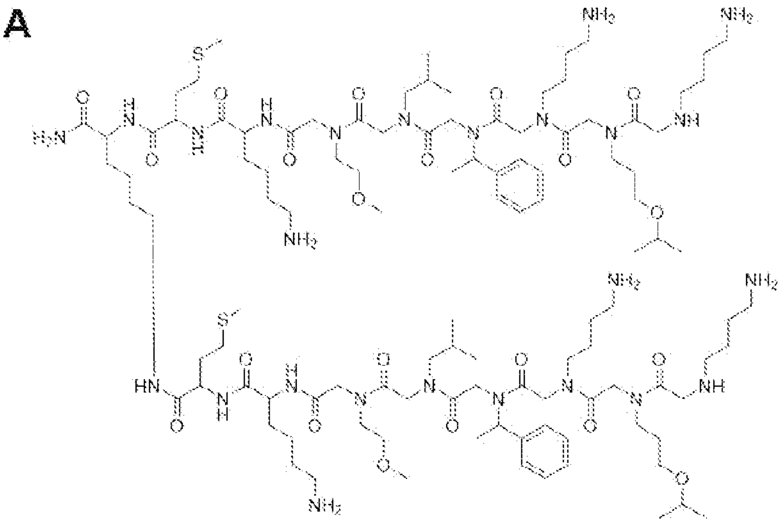
FIG. 9 shows chemical structures of derivatives of TRBP6, namely (A) dimer, (B) trimer, (C) tetramer, and (D) cyclic dimer, in accordance with preferred embodiments described herein.
Figure 9B:
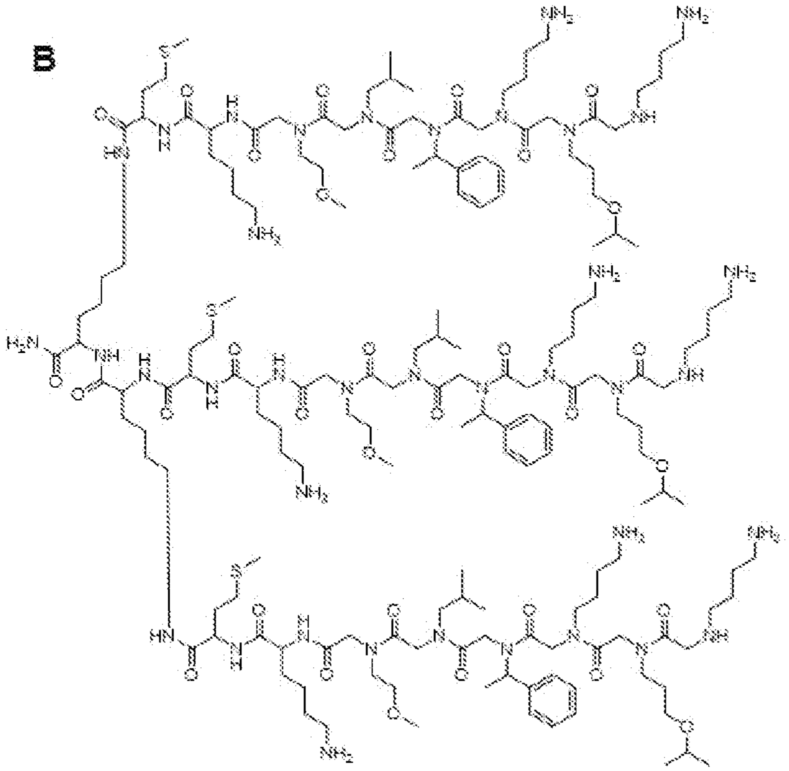
Figure 9C:
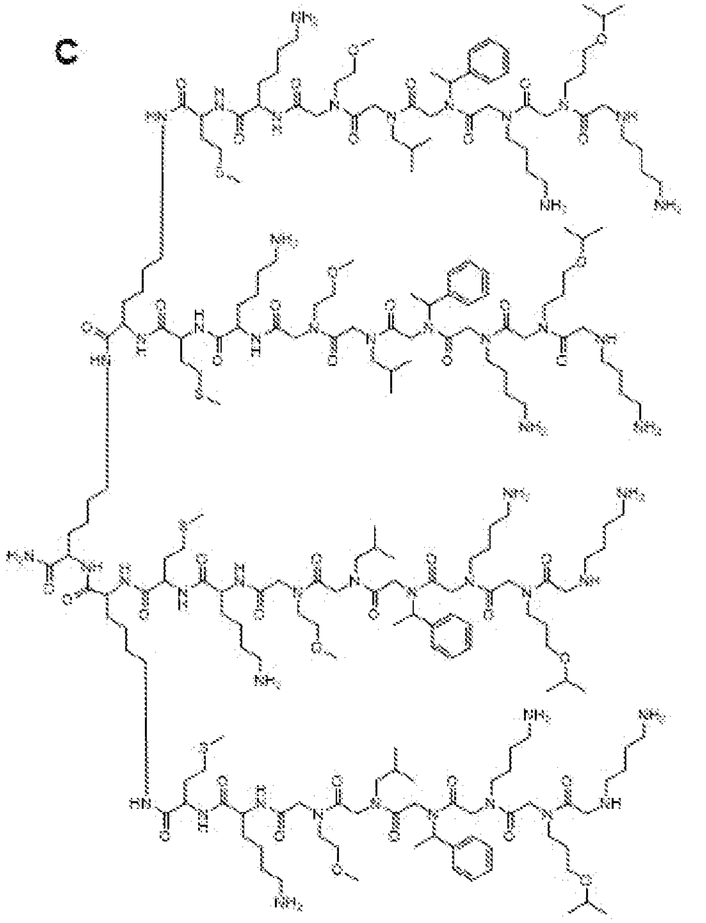
Figure 9D:
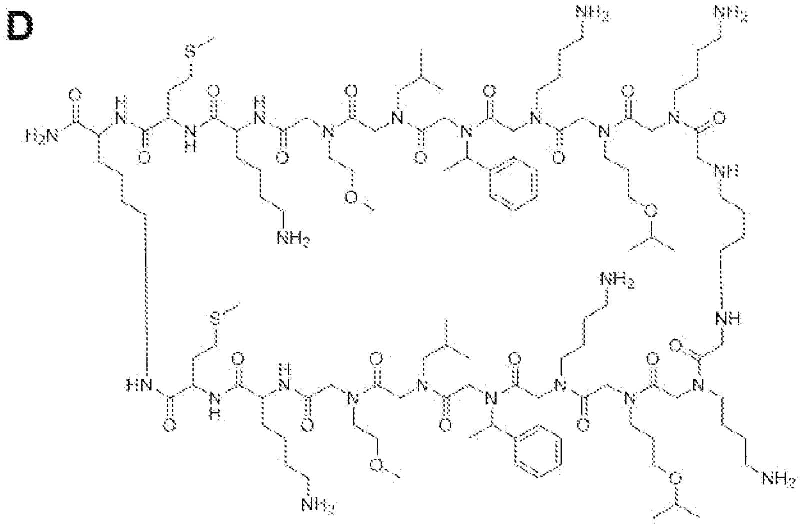

FIG. 8 shows IVIS imaging of the fluorescence intensity of mice injected with an exemplary compound capable of crossing the BBB, Cy5.5-TRBP3, at 5, 15, and 30 minutes, and 30 minutes ex vivo after perfusion.

EXAMPLE 2

Solubility in Water.

Solubility of TRBP-6 peptoid was determined by titration. Briefly, a precise amount (5 mg) of TRBP-6 was measured in a transparent 1.5 ml Eppendorf tube. DI water was added dropwise (~5 μl/drop) into the tube until the solids were completely dissolved and the solution was clear. Solubility was calculated as the ratio of quantity of peptoid and the total volume of DI water. At 4.96 mg in 10 μl (496 mg/ml) concentration, TRBP-6 remains completely soluble. Hence, the water solubility of TRBP-6 was considered higher than 496 mg/ml, highly water soluble. The solubility of TRBP6 in water is shown below.

| Compound | $t_R$ (min) | Solubility |
|---|---|---|
| TRBP-6 | 4.904 | >496 mg/ml |

Figure 10:
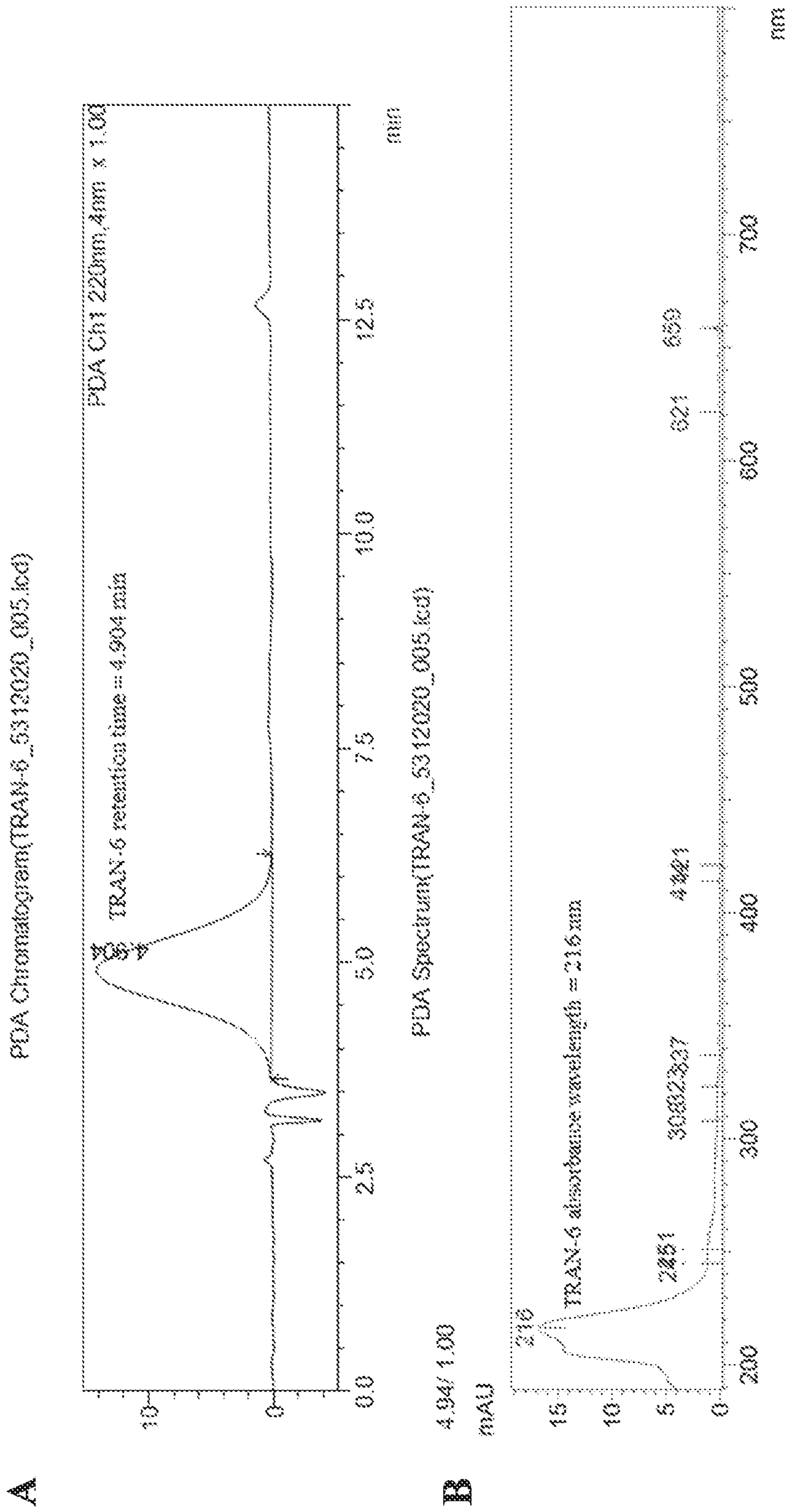
FIG. 10 shows HPLC chromatograms for TRBP6, namely (A) PDA Chromatogram, and (B) PDA Spectrum.

HPLC Analysis. RP-HPLC was conducted on an LC-20A liquid chromatographic system (Shimadzu, Japan). In detail, the HPLC system consisted of a Shimadzu LC-20AD solvent delivery pump, a SIL-20A auto-sampler, and a Shimadzu SPD-M20A UV/Vis detector. The TRBP-6 peptoid was analyzed using a Phenomenex® HPLC C18 column (250×4.6 mm, 5 μm) at room temperature. The mobile phase was composed of solvent A (0.1% TFA in water) and solvent B (0.1% TFA in acetonitrile, TFA: trifluoroacetic acid). An aliquot of 10 μl of TRBP-6 peptoid solution (350 μg/ml in ACN:$H_2O$, 1:1) was injected into HPLC system. An isocratic method with flow rate of 1 ml/min was applied in 30% B for 15 min for TRBP-6. The detection wavelength was set to 220 nm. The data was acquired and processed with LabSolutions version 5.92. HPLC chromatograms for TRBP-6 are shown in FIG. 10, namely (A) PDA Chromatogram, and (B) PDA Spectrum. FIG. 10(A) is a RP-HPLC chromatogram of TRBP-6 (retention time $t_R$=4.904 min) obtained by above HPLC method to illustrate the purity of the synthesized TRBP-6. FIG. 10(B) is a plot of UV absorbance spectrum of TRBP-6 obtained from injecting TRBP-6 into the HPLC column to show the wavelength of maximum UV absorbance of TRBP-6 ($\lambda_{max}$=216 nm).

Stability in PBS pH 7.4.

TRBP-6 peptoid was diluted with PBS pH 7.4 to 350 μg/ml. The solution was incubated in the water bath at 37° C. with gentle shaking. The aliquots (50 μl) were withdrawn from the TRBP-6 solution at different time intervals (0, 1, 3, 6, 9, 24 h). At each time point, 10 μl of solution was injected into HPLC for analysis. To examine the reproducibility, the experiments were carried out in triplicate. The table below shows the content of the TRBP-6 peptoid in PBS pH 7.4 at different time intervals.

Stability in Human Plasma.

TRBP-6 peptoid solution with a concentration of 5 mg/ml in PBS was diluted to 1.4 mg/ml by human plasma. After incubation at 37° C. in human plasma for 0, 1, 3, 6, 9 and 24 h, 50 μl of the mixture was quenched with 150 μl of cold acetonitrile and centrifuged at 148000 rpm×20 min. The supernatant (100 μl) was detected by HPLC. The assay was performed in triplicates. The table below shows the content of TRBP-6 peptoid in human plasma at different time intervals. The data support the excellent stability of TRBP-6.

| Time (h) | TRBP-6 amount remains (%) in PBS pH 7.4 | TRBP-6 amount remains (%) in human plasma |
|---|---|---|
| 0 | 100.0 ± 2.4 | 100.0 ± 1.2 |
| 1 | 98.9 ± 6.5 | 99.5 ± 3.5 |
| 3 | 95.5 ± 3.3 | 94.0 ± 2.1 |
| 6 | 94.6 ± 2.3 | 93.0 ± 5.3 |
| 9 | 92.7 ± 0.2 | 92.0 ± 2.9 |
| 24 | 91.3 ± 3.8 | 90.3 ± 4.7 |

Figure 11:
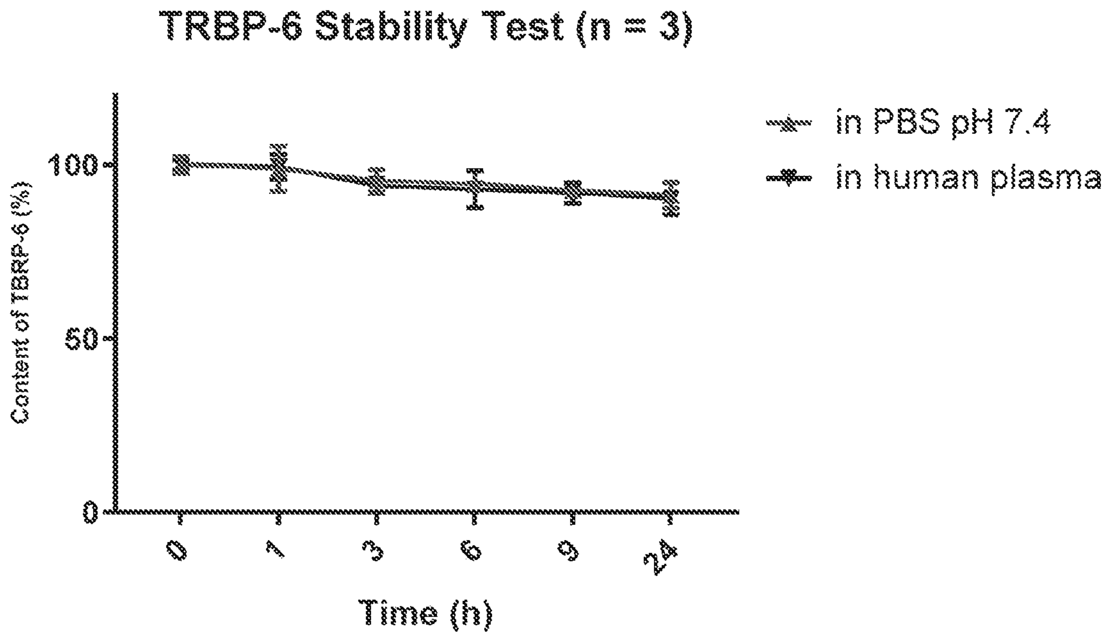
FIG. 11 shows the stability of the TRBP-6 peptoid in PBS pH 7.4 and in human plasma (n=3) at different time intervals.

FIG. 11 shows the stability of the TRBP-6 peptoid in PBS pH 7.4 and in human plasma (n=3) at different time intervals.

What is claimed is:

1. A method for the delivery of an agent to the brain in a subject comprising administering a pharmaceutical composition to the subject, wherein the pharmaceutical composition comprises a pharmaceutically acceptable excipient, carrier, buffer, stabilizer, or mixture thereof, wherein the composition comprises a compound capable of crossing the blood-brain barrier and an agent, wherein the compound is linked to the agent, and wherein the compound has a structure of:

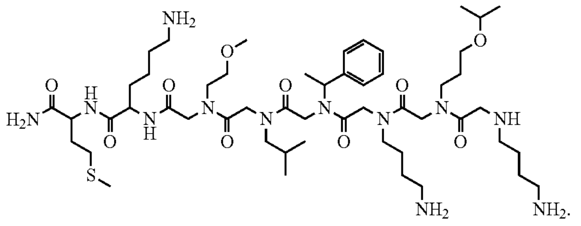 [SMILES: COCCN(CC(=O)NC(CCCCN)C(=O)NC(CCSC)C(N)=O)C(=O)CN(CC(C)C)C(=O)CN(C(=O)CN(CCCCN)C(=O)CN(CCCOC(C)C)C(=O)CNCCCCN)C(C)c1ccccc1]

2. The method of claim 1, wherein the subject has a disease or disorder of the brain, and wherein the disease or disorder of the brain is cancer, ischemic stroke, Alzheimer's disease, or Parkinson's disease.

* * * * *

SEQUENCE LISTING

```
<160> NUMBER OF SEQ ID NOS: 1

<210> SEQ ID NO 1
<211> LENGTH: 20
<212> TYPE: PRT
<213> ORGANISM: Artificial Sequence
<220> FEATURE:
<223> OTHER INFORMATION: Angiopep-2 peptide (Ang) with terminal cysteine

<400> SEQUENCE: 1

Thr Phe Phe Tyr Gly Gly Ser Arg Gly Lys Arg Asn Asn Phe Lys Thr
1               5                   10                  15

Glu Glu Tyr Cys
            20
```